United States Patent [19]

Godsey

[11] Patent Number: 4,761,378
[45] Date of Patent: Aug. 2, 1988

[54] MICROBIOLOGICAL TESTING APPARATUS

[75] Inventor: James H. Godsey, Roseville, Calif.

[73] Assignee: American Home Products Corp. (Del.), New York, N.Y.

[21] Appl. No.: 472,416

[22] Filed: Mar. 4, 1983

[51] Int. Cl.$^4$ .............................................. C12M 1/20
[52] U.S. Cl. .................................... 435/293; 422/102; 435/33; 435/34; 435/298; 435/300; 435/301; 435/310; 436/809
[58] Field of Search ............... 435/284, 293, 297, 298, 435/300, 301, 310, 34, 33; 422/58, 102, 104; 436/809

[56] References Cited

U.S. PATENT DOCUMENTS

| | | | |
|---|---|---|---|
| 3,356,462 | 12/1967 | Cooke et al. | 422/102 |
| 3,713,985 | 1/1973 | Astle | 435/301 |
| 3,957,583 | 5/1976 | Gibson et al. | 435/34 X |
| 4,012,288 | 3/1977 | Lyman et al. | 435/284 |
| 4,038,149 | 7/1977 | Liner et al. | 435/300 |
| 4,038,151 | 7/1977 | Fadler et al. | 435/301 |
| 4,056,359 | 11/1977 | Janin | 435/301 |
| 4,154,795 | 5/1979 | Thorne | 435/300 |
| 4,284,725 | 8/1981 | Fennel, III et al. | 435/301 |
| 4,292,273 | 9/1981 | Butz et al. | 435/301 X |
| 4,349,275 | 9/1982 | Ayotte et al. | 422/104 X |

Primary Examiner—Sidney Marantz
Attorney, Agent, or Firm—Adley F. Mandel

[57] ABSTRACT

An improved microbiological test tray is described which are provided with fasteners so that two or more of the trays may be joined together for ease in inoculation, incubation, lyophilization and reading. In another aspect of the invention an improved tray structure is described which provides openings for the flow of vapor during the lyophilization step so that a greater number of trays may be lyophilized at the same time and also that lyophilization may be carried out in a shorter period of time due to the improved vapor flow. In another aspect of the invention an improved test card is described in which the API 20 test strip is reshaped into a card of two rows of ten cupules conforming to the same pattern as other frequently used test trays. A holder tray is provided for the card and the holder is provided with connecting fasteners so that it and the test card may be joined into one or more additional test trays for ease in inoculation, incubation and reading. In still another aspect of the invention improved templates are described for use with multiply connected trays.

12 Claims, 5 Drawing Sheets

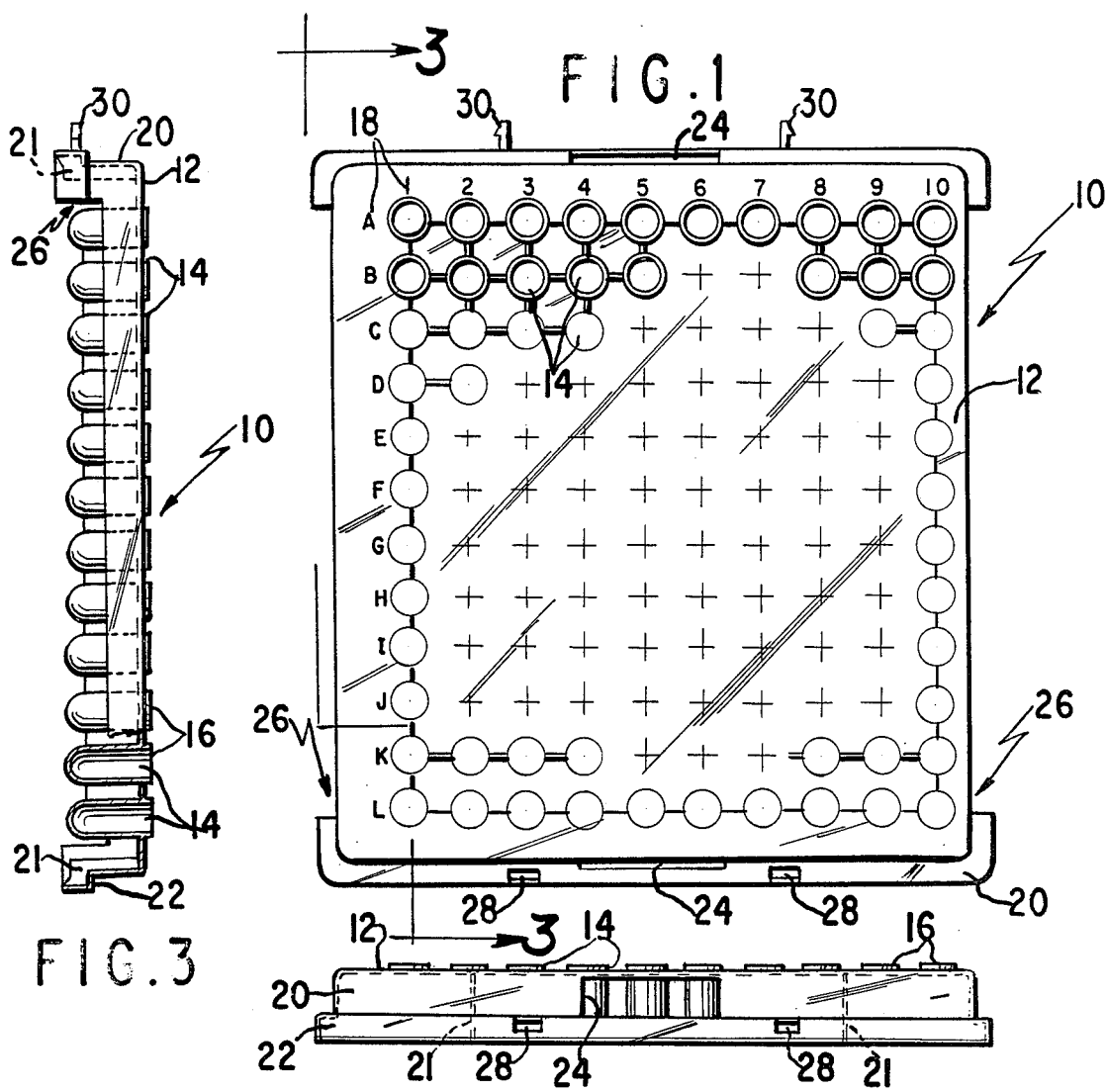
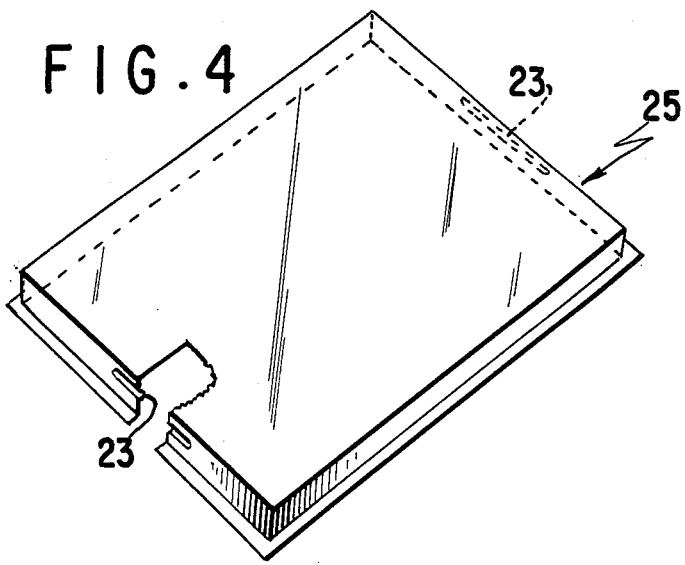
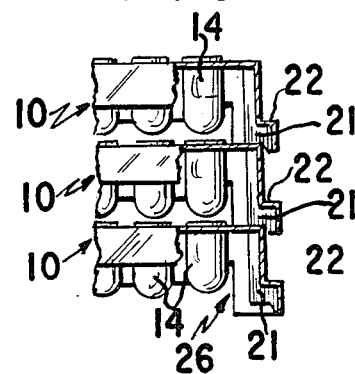

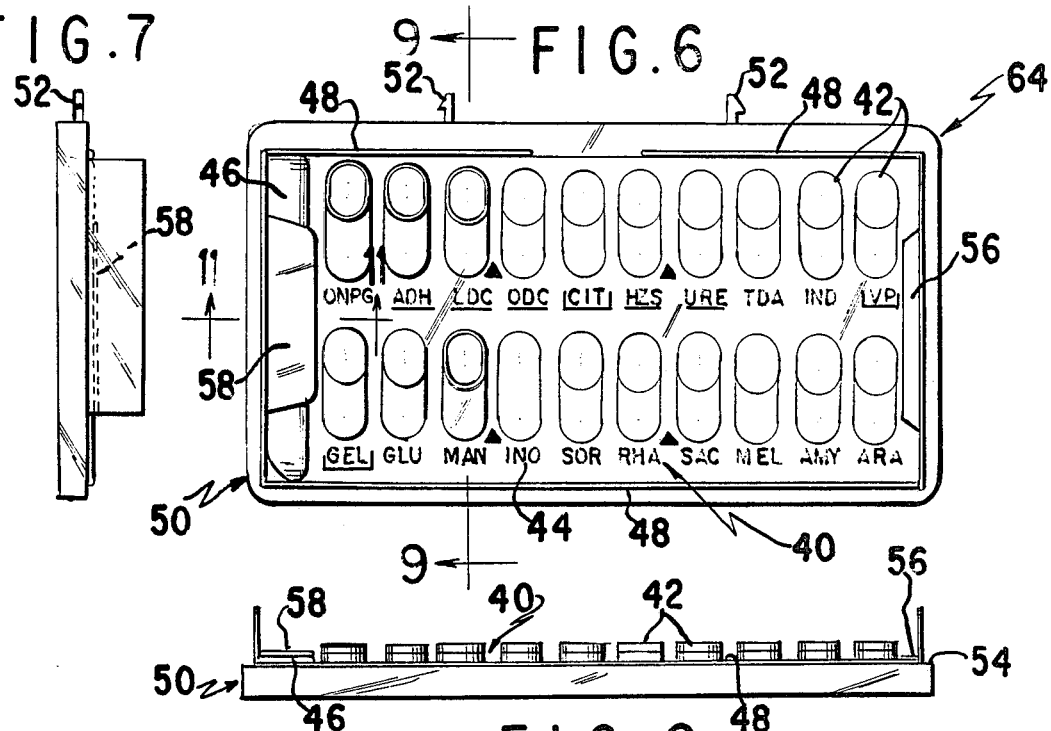
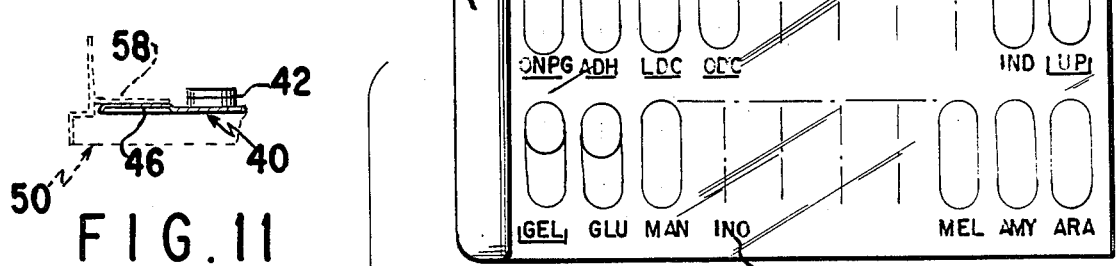
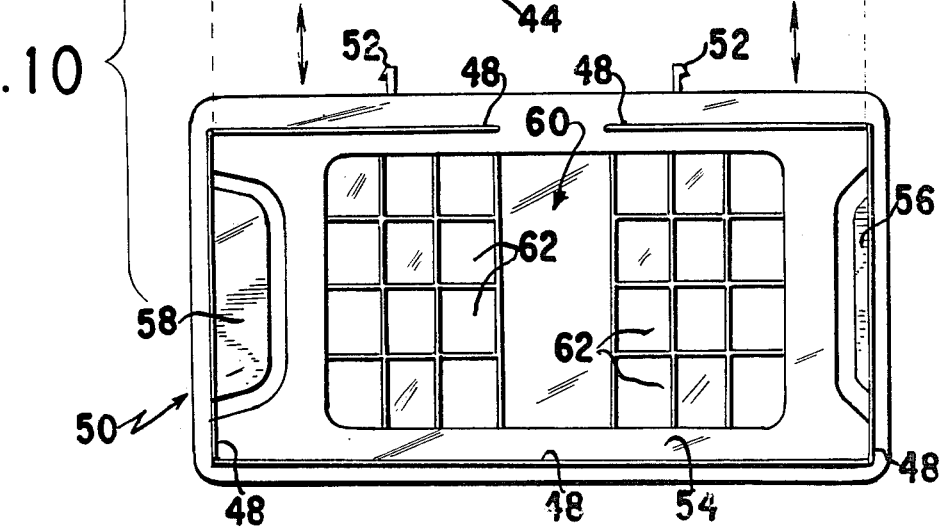

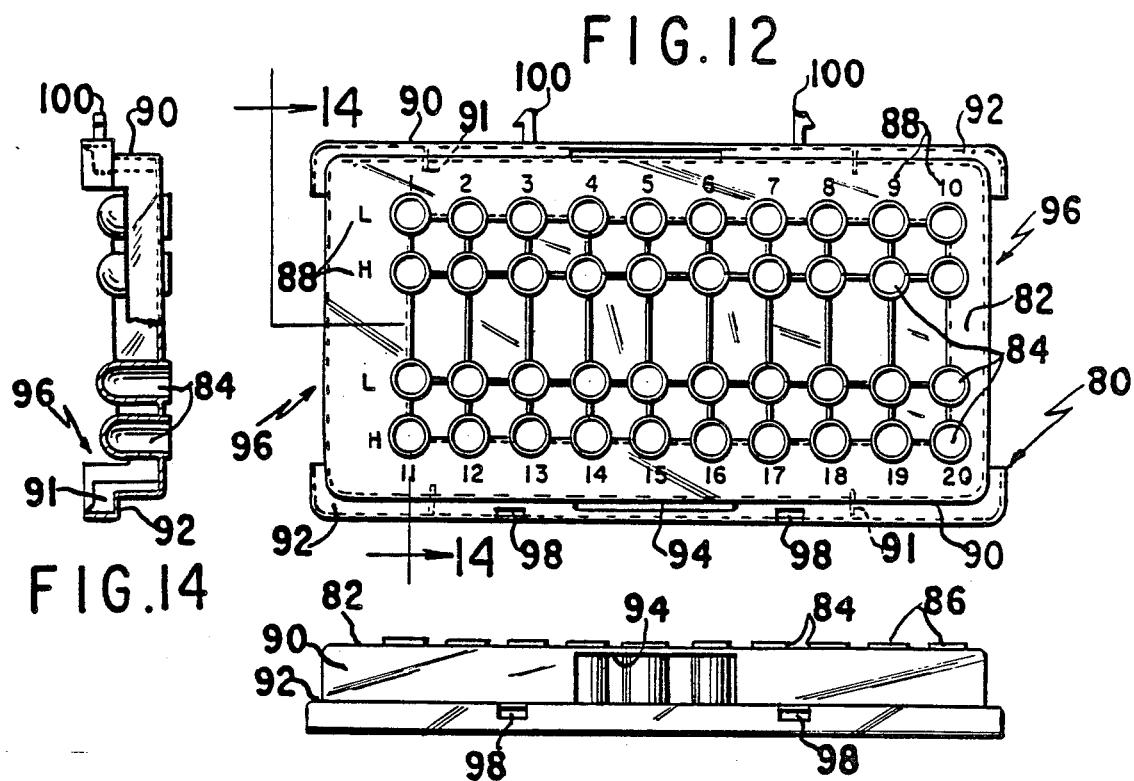
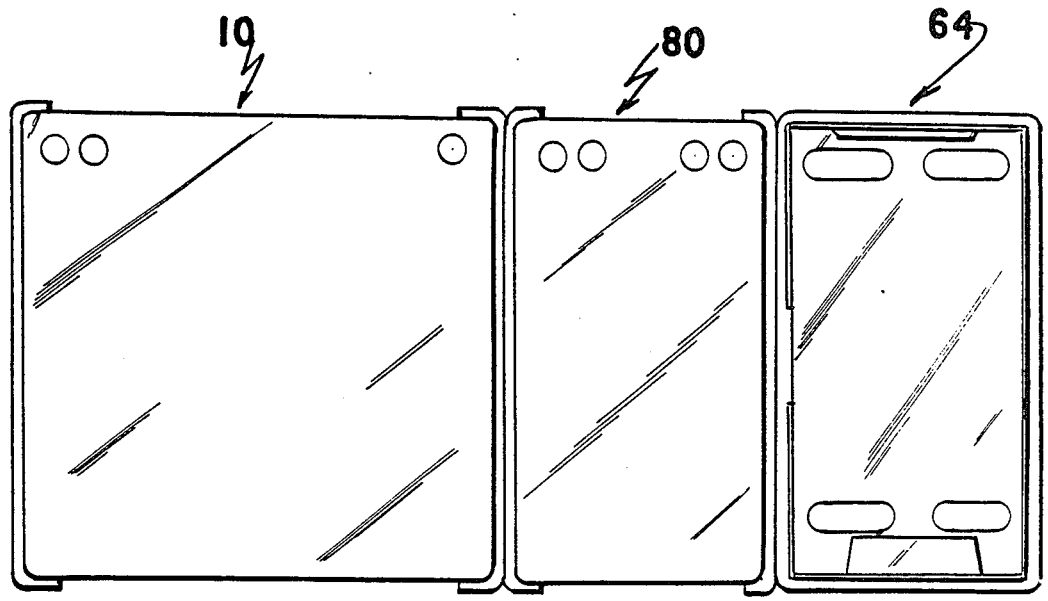

MICROBIOLOGICAL TESTING APPARATUS

This application relates to microbiological testing apparatus. More particularly it relates to improved microbiological test trays which are to be read in either a manual or an automatic reader.

A number of different types of microbiological testing are carried out in trays which have a number of chambers which are prepared by the manufacturer to contain test reagents in them. The chambers are also known as test wells or cupules. Typically the test reagents are complex chemicals which in the presence of an active fermenting culture change color, become cloudy or otherwide indicate that fermentation is or has taken place. The absence of an indication of such activity is a negative result which can be as significant as a positive result in the identification of unknown microorganisms or in determining the susceptibility of a microorganism for attack by an antibiotic. Also such test trays are used to determine what microorganism is causing the illness of a patient.

Typically the test reagents are charged into the chambers in the form of an aqueous solution and any growth medium may also be charged at the same time. Typically a different combination of reagent or growth medium is charged into different chambers so that a great number of individual reactions are performed in a physically small apparatus.

After charging the test trays are placed into a lyophilizer where the ingredients are first frozen and then the water is removed by sublimation upon the lowering of the ambient pressure to form a vacuum. It is the test tray containing the dried reagents which is sold and used for carrying out microbiological tests. When a test is to be performed a microorganism is inoculated into each of the test chambers with sufficient water to reconstitute the reagents. The test tray is then incubated at an appropriate temperature, usually elevated above ambient, for an extended period of time. After a predetermined period the individual chambers are examined for the presence or absence of a reaction or an indication of color change, or a change in turbidity. While these chambers may be read visually by a technician there have been developed a number of reading machines which facilitate the reading of the trays and result in the saving of technicians' time.

A typical tray may contain 20 to 120 chambers for individual reactions. As the tests have grown more complex more chambers are needed. Also different test trays are used to determine different characteristics of the microorganisms. While trays can be read individually, each requires the use of technicians' time in the preparation, inoculation, incubation and reading of the results.

One of the standard tests is described in U.S. Pat. Nos. 3,936,356 and 4,056,359. In this patent is described a 20 cupule test strip in which a single row of 20 cupules is arranged side by side each containing a different reagent. By reading the cupules in which reactions occur an unknown microorganism can be identified with reference to a manual of reactions.

The nature of the cupules and their use in microbiological testing is described in U.S. Pats. Nos. 3,854,883 and 3,876,378 and 4,208,480.

A typical automatic reader is manufactured by Dynatech Corporation, Alexandria, Va. as model MR 600. A typical manual reader is made by Bellco Glass, Inc., Vineland, N.J.

It is an object of the present invention to provide improved test trays which may be coupled together to form a single unit for carrying out a number of different reactions at the same time.

It is another object of the invention to provide improved microbiological test trays in which the processing steps, particularly inoculation and lyophilization, may be carried out in larger numbers with a resultant saving in technicians' time.

It is yet another object of the invention to provide a modified form of the API 20 test strip for use in connection with other test trays.

BRIEF DESCRIPTION OF THE DRAWINGS

Further objects of the invention will be apparent from reading the following description in conjunction with the drawings in which:

FIG. 1 is a top view of a 120 chamber microbiological test tray;

FIG. 2 is a rear view of the tray of FIG. 1;

FIG. 3 is a left side view of the tray of FIG. 1; the right side view being a mirror image thereof;

FIG. 4 is a perspective view of a cover for the tray of FIG. 1;

FIG. 5 is a partial elevational view of a plurality of the trays of FIG. 1 stacked one on top of the other;

FIG. 6 is a top view of a 20 cupule microbiological test card; combined with its holder;

FIG. 7 is a left side view of the combination of FIG. 6;

FIG. 8 is a rear view of the combination of FIG. 6;

FIG. 9 is a sectional view taken generally along line 9—9 of FIG. 6;

FIG. 10 is an exploded top view showing separately the components of the combination of FIG. 6;

FIG. 11 is a partial sectional view taken generally along line 11—11 of FIG. 6;

FIG. 12 is a top view of a 40 chamber microbiological test tray;

FIG. 13 is a rear view of the tray of FIG. 12;

FIG. 14 is a left side view of the tray of FIG. 12 taken partly in section along lines 14—14 of FIG. 12

FIG. 15 is a top view of the trays of FIGS. 1, 6 and 12 joined together;

Figure 16:
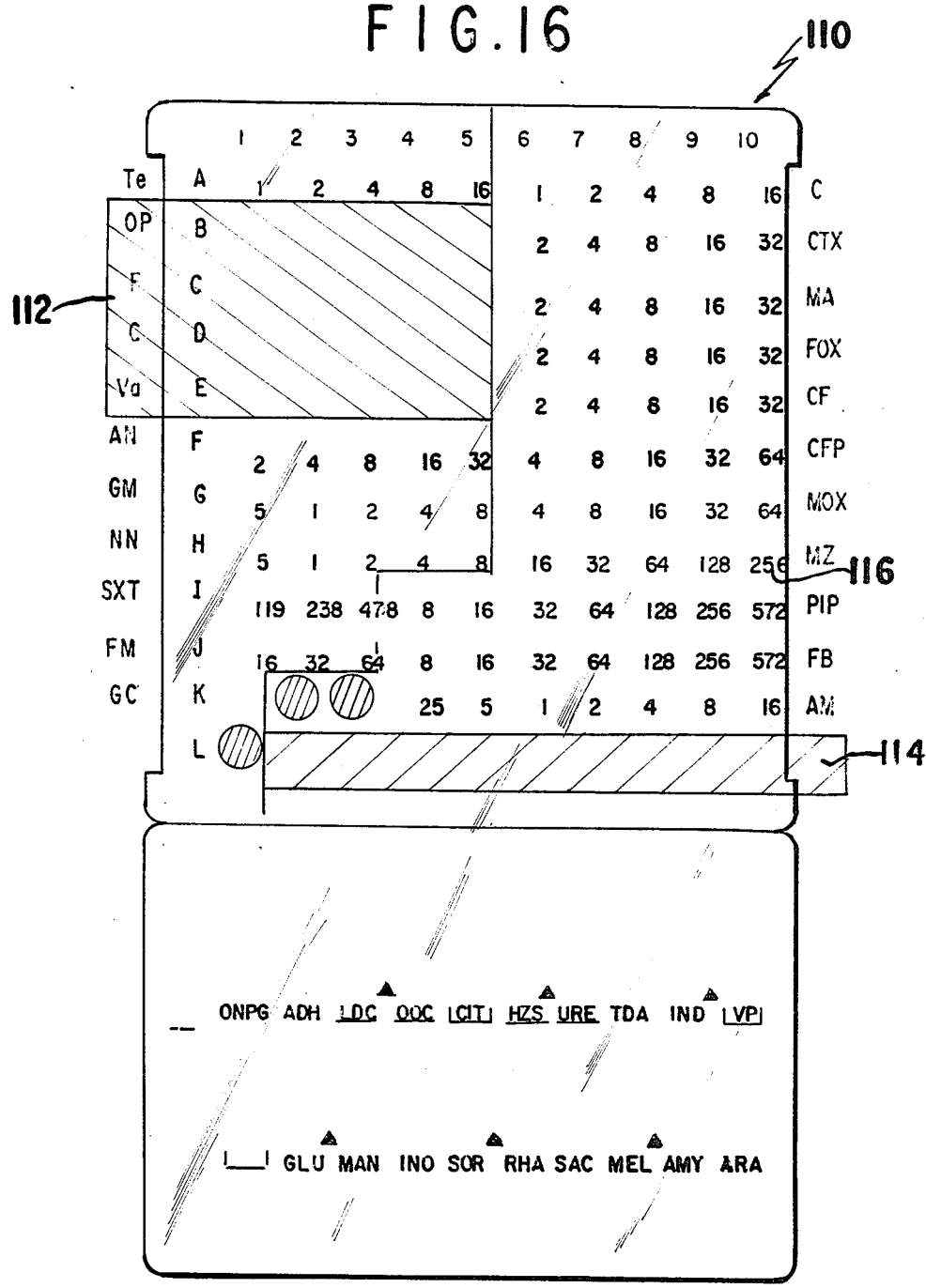
FIG. 16 is a top view of a template.

The objects of the invention may be accomplished with a biological test tray having a shouldered skirt around its periphery. A portion of the skirt is cutaway to provide an opening to permit vapor flow during lyophilization. The skirt is also provided with fastening devices so that two of the trays may be joined together. The API 20 test strip is modified from a single row of 20 cupules to a card having two rows of ten cupules. A holder is provided for the card so that it may be connected to other test trays having ten chambers in a row.

As shown in FIGS. 1, 2, and 3 a biological test tray 10 has supported in its upper surface 12 a plurality of chambers 14 the upper rims 16 of which extend slightly above the upper surface 12. Indicia 18 are applied at the end of each row and column in order to specify a particular chamber. Surrounding the tray is a skirt 20 which extends downwardly from the upper surface and has a shoulder 22 and lugs 21 formed in it. The shoulder, lug and skirt combination permit the stacking of the trays one on top of the other during processing.

It has been found desirable to cutaway a portion 26 at opposite sides of the skirt in order to permit vapor flow during lyophilization. The size of the opening thus provided is not critical provided it is above the minimum necessary for effective flow. An orifice 24 is provided on opposite sides of the tray to cooperate with a snap-on fastener 23 on a cover 25 (FIG. 4) over the tray and skirt. The orifice 24 shown is equal in height to the diameter of the chambers and is four times as long as the diameter of the chambers.

The test trays preferably are used in conjunction with an automatic reading machine. For some tests it is desirable to have more than the 120 chambers shown with the same or different ingredients. For convenience in processing such as simultaneous inoculation, incubation and reading it has been found desirable to join two trays together for this purpose. Openings 28 are provided to receive a male snap fastener attached to a second tray as will be described below. If desired, male fasteners 30 may also be attached to the tray skirt opposite the openings 28 to provide for connection of more than two trays. The design of the fasteners and openings is not critical, and any well known combination of stud and opening may be used for the purpose. The trays are preferably made of a slightly flexible plastic which imparts sufficient flexibility to the male fasteners 30 to be engaged and disengaged in the openings 28.

In U.S. Pat. No. 4,056,359 assigned to Analytab Products Inc. and herein incorporated by reference, there is described apparatus for identifying bacteria. In FIG. 1 of the U.S. Pat. No. 4,056,359 patent there is shown a biological test strip of twenty individual reaction chambers. As is shown in FIG. 1 the test plate (11) comprises a plurality of small identified reaction chambers (12) (identified by number for example) disposed linearly along the strip. As is shown in FIG. 2, the strip is conveniently formed attaching two molded plastic strips 13 and 14 so as to form individual compartments 15. The test strip is known in the art as the "API 20".

FIGS. 6–11 show a version of the test strip which has been modified into the form of a card 40. The card is formed from two molded plastic strips joined together to form twenty individual chambers. If desired, indicia, 44 may be associated with each cupule in order to identify its contents. Preferably, the indicia correspond with identification standards promulgated by the National Committee for Clinical Laboratory Standards which are incorporated herein by reference. The cupules are arranged in two rows of ten in order to cooperate and align with the ten rows of the tray shown in FIG. 1.

A tray 50 is provided to hold the card 40 in a combination 64 and has provided on it male fasteners 52 which may engage the openings 28 of the tray in order to secure the card 40 and the tray 50 to the tray 10. The tray 50 is made of a clear plastic material having a base portion 54, to which the fasteners 52 are attached and retaining arms 56,58, which extend over the ends of the card 40 to hold it in position. Retaining arm 58 is wider than the retaining arm 56 so that the card 40 can be inserted only in one orientation, the orientation being provided by the indexing portion 46 which is a wide portion at one end only of the card 40. As is shown in FIG. 11 the indexing portion may be dished or thickened for a friction fit. A ridge 48 is provided to retain the card 40 in the tray 50. Other additional retaining devices and structural members may be added to provide rigidity and aid registry.

It has also been found desirable to provide recessed portion 60 which is divided into a series of recessed chambers 62. In use these chambers may contain water to provide humidification which is desirable during incubation. The card 40 is above the recessed portion 60 when in place in the tray 50.

In FIGS. 12–14 as shown an alternate biological test tray 80 having an upper surface 82 and forty chambers 84 arranged in four rows of ten with the upper rims 86 extending slightly above the upper surface 82. Indicia 88 are preferably associated with each chamber. A skirt 90 surrounds the test tray and is attached to the upper surface 82. A shoulder 92 and lugs 91 are formed in the skirt for convenience in stacking during processing. It has been found advantageous to have a cutaway portion 96 of the skirt at opposite ends as described above with reference to cutaway portion 26 of tray 10. Openings 98 are formed on the skirt on one side and are adapted to connect with fasteners on other trays. Male fasteners 100 may be formed on the opposite side of the skirt for connection to other trays having female openings. A cover (not shown) similar to cover 25 may be fitted over the tray and skirt to cover the chambers. Orifices 94 are provided to receive a snap fastener portion of the cover and hold it in place.

Figure 17:
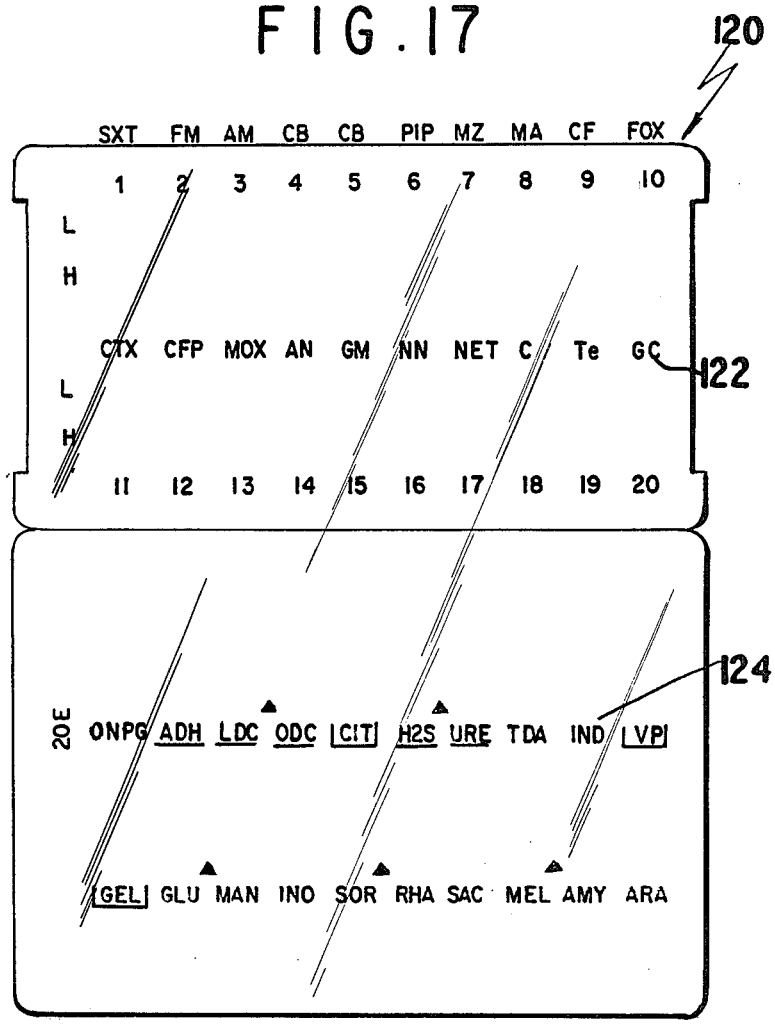
FIG. 17 is a top view of an alternate template.

Not all of the chambers need be read for all tests performed. It is therefore advantageous to provide templates which indicate those selected chambers which are to be read in order to obtain the results for a particular test. Typical templates 110 and 120 are shown in FIGS. 16 and 17 and are typically a transparent plastic sheet of the same size as the combination of trays which are to be read. The areas 112 and 114 may be made opaque to exclude chambers that are not to be read in the test associated with the template 110. Indicia 116, 122, 124 may be present for ease in reading. The present invention by use of a number of trays coupled together permits the use of templates of larger size in which the selected chambers from more than one test tray may be read at the same time. It is the rigidity of the connection between the individual microbiological test trays which permits the use of precut templates with the test trays.

What is claimed is:

1. In a biological test tray having a plurality of chambers for carrying out tests of microorganisms in the presence of a plurality of different reagents in which the reagents are inserted into the chambers in a solution and then lyophilized to dryness, the improvement comprising A. a skirt around the periphery of the tray whereby a plurality of said trays may be stacked in a lyophilizer without closing said chambers and, B. an orifice formed in at least two sides of said skirt whereby evacuation of sublimed moisture is enhanced.

2. A tray as defined in claim 1 wherein said orifices are formed in said skirt on opposite sides of said tray.

3. A tray as defined in claim 1 wherein the width each of said orifices is about equal to the diameter of one of the chambers and the length of said orifice is about four times the diameter of one of the chambers.

4. The test tray of claim 1 further comprising cutaway portions formed in said skirt on sides of the tray not containing the orifices.

5. In a biological test tray having a plurality of chambers for carrying out tests of microorganisms in the presence of a plurality of different reagents in which the reagents are inserted into the chambers in a solution and then lyophilized to dryness, a microorganism is inoculated into each of said chambers and incubated for a predetermined period, and the activity of said microorganisms is read in an automatic reader, the improvement comprising
- A. a skirt around the periphery of the tray whereby a plurality of said trays may be stacked in a lyophilizer without closing said chambers,
- B. an orifice formed in at least two sides of said skirt whereby evacuation of sublimed moisture is enhanced, and
- C. cooperating fasteners defined on said skirt, whereby a plurality of said trays may be joined together for inoculation, incubation and reading.

6. The test tray as defined in claim 5 further comprising a cover adapted to fit over the top of said skirts and cover said chambers.

7. The biological test tray as defined in claim 5 connected to at least one other tray.

8. The biological test tray as defined in claim 7 further comprising a template adapted to cooperate with said chambers during evaluation on an automatic reader.

9. A holder for a biological test card comprising
- A. a base
- B. retaining means comprising a pair of retaining arms of unequal width connected to said base adapted to receive a biological test card in only one orientation, and
- C. fastener means coupled to said base and extending outwardly from said base and adapted to cooperate with a biological test tray having cooperating fasteners defined on the skirt of said tray.

10. The holder of claim 9 wherein said retaining means include a ridge adapted to retain the test card in the holder.

11. The holder of claim 9 further comprising a recessed portion in the base adapted to contain water and said recessed portion being below a biological test card when in place in the holder.

12. A microbiological test card comprising
- A. two molded plastic strips joined together to form twenty individual chambers arranged in two rows of ten chambers each;
- B. a dehydrated reagent in each of said chambers; and
- C. orientation means comprising an indexing portion which is wide on one end only of the card whereby said card can be placed into a holder for the biological test card in only one orientation, said holder comprising a base, retaining means connected to the base and adapted to cooperate with the test card, and fastener means coupled to the base of the holder adapted to cooperate with a biological test tray.

* * * * *